(12) United States Patent
Huang

(10) Patent No.: US 11,786,405 B2
(45) Date of Patent: Oct. 17, 2023

(54) COMBINED GOGGLE AND FACE MASK

(71) Applicant: OURAD SAFETY CO., LTD., Tainan (TW)

(72) Inventor: Pin-Tsung Huang, Tainan (TW)

(73) Assignee: Ourad Safety Co., Ltd., Tainan (TW)

( * ) Notice: Subject to any disclaimer, the term of this patent is extended or adjusted under 35 U.S.C. 154(b) by 155 days.

(21) Appl. No.: 17/382,768

(22) Filed: Jul. 22, 2021

(65) Prior Publication Data

US 2023/0028543 A1    Jan. 26, 2023

(51) Int. Cl.
*A61F 9/02* (2006.01)
*A41D 13/11* (2006.01)
*A42B 3/20* (2006.01)

(52) U.S. Cl.
CPC .......... *A61F 9/029* (2013.01); *A41D 13/1184* (2013.01); *A42B 3/20* (2013.01); *A61F 9/027* (2013.01)

(58) Field of Classification Search
CPC . A61F 9/027; A61F 9/029; A42B 3/20; A41D 13/1184; A63B 33/002; A63B 33/004; A63B 33/006; A63B 33/008
See application file for complete search history.

(56) References Cited

U.S. PATENT DOCUMENTS

| | | | | |
|---|---|---|---|---|
| 4,250,577 A * | 2/1981 | Smith | .......... | A62B 18/084 2/427 |
| 4,653,124 A * | 3/1987 | McNeal | .......... | A61F 9/029 2/427 |
| 6,349,419 B1 * | 2/2002 | Chiang | .......... | A63B 33/004 2/452 |
| 6,381,749 B1 * | 5/2002 | Cyr | .......... | A42B 3/20 2/427 |
| 6,886,183 B2 * | 5/2005 | DeHaan | .......... | A42B 3/20 2/6.7 |
| 6,948,813 B2 * | 9/2005 | Parks | .......... | A61F 9/025 351/158 |
| 6,957,447 B1 * | 10/2005 | Broersma | .......... | A63B 71/10 2/427 |
| 7,168,095 B2 * | 1/2007 | Wright | .......... | A41D 13/11 2/430 |

(Continued)

FOREIGN PATENT DOCUMENTS

| TW | M573221 U | 1/2019 |
|---|---|---|
| TW | M605535 U | 12/2020 |

*Primary Examiner* — F Griffin Hall
(74) *Attorney, Agent, or Firm* — Rosenberg, Klein & Lee

(57) ABSTRACT

A combined goggle and face mask includes a goggle body, a strap, a shield, and two retaining members. Either side of the goggle body is recessed with a receiving portion. The goggle body is provided with a lens. Either end of the strap is provided with a bracket to be coupled to the receiving portion. The bracket is supported by the receiving portion. The shield is coupled to the google body. The retaining member is coupled to the bracket. Because the bracket is received in the receiving portion, the bracket can be supported by the receiving portion, so as to offset the pulling force. First edges that are oblique edges and second edges each in the form of a curved corner of the bracket are supported by two oblique sides and two bent sides each in the form of a curved corner of the receiving portion.

7 Claims, 12 Drawing Sheets

(56) References Cited

U.S. PATENT DOCUMENTS

| | | | | |
|---|---|---|---|---|
| 7,320,144 B2* | 1/2008 | Katz | A42B 3/185 | |
| | | | 2/9 | |
| 7,882,575 B2* | 2/2011 | Wang-Lee | A61F 9/027 | |
| | | | 2/431 | |
| 7,895,680 B2* | 3/2011 | Anderson | A42B 3/18 | |
| | | | 2/427 | |
| 8,104,095 B2* | 1/2012 | Cyr | A41D 13/1184 | |
| | | | 2/9 | |
| 8,225,431 B2* | 7/2012 | Cyr | A42B 3/22 | |
| | | | 2/6.3 | |
| 8,549,672 B2* | 10/2013 | Stevens | A61F 9/029 | |
| | | | 2/427 | |
| 9,504,287 B1* | 11/2016 | Guffin, III | A61F 9/026 | |
| 9,629,751 B2* | 4/2017 | Chen | A61F 9/027 | |
| 9,693,596 B2* | 7/2017 | Huffman | A42B 3/20 | |
| 9,861,529 B2* | 1/2018 | Seo | A61F 9/022 | |
| 11,096,827 B1* | 8/2021 | Kono | G02C 11/08 | |
| 2004/0111779 A1* | 6/2004 | Gagnon | A42B 3/20 | |
| | | | 2/9 | |
| 2006/0085883 A1* | 4/2006 | Tan | A41D 13/1107 | |
| | | | 2/427 | |
| 2007/0186324 A1* | 8/2007 | Sheldon | A42B 3/20 | |
| | | | 2/9 | |
| 2007/0192946 A1* | 8/2007 | Wright | A61F 9/045 | |
| | | | 2/424 | |
| 2008/0127400 A1* | 6/2008 | Dupuis | F41H 1/02 | |
| | | | 2/9 | |
| 2008/0134417 A1* | 6/2008 | Aoyama | A61F 9/027 | |
| | | | 2/431 | |
| 2009/0113590 A1* | 5/2009 | Lian | A63B 71/10 | |
| | | | 2/9 | |
| 2009/0113607 A1* | 5/2009 | Lian | A41D 13/1184 | |
| | | | 2/427 | |
| 2020/0368068 A1* | 11/2020 | Wu | A61F 9/067 | |

* cited by examiner

COMBINED GOGGLE AND FACE MASK

FIELD OF THE INVENTION

The present invention relates to a combined goggle and face mask, which can avoid breaking or cracking due to a pulling force, so as to ensure the overall integrity.

BACKGROUND OF THE INVENTION

In general, a protective goggle or face shield is equipped with a strap so that it can be held on a user's head. For example, Taiwan Utility Model Publication No. M573221 published on Jan. 21, 2019 discloses a goggle structure, comprising a frame having a frame portion and a cushion portion. A plurality of first stop blocks and a plurality of second stop blocks are arranged on the periphery of the frame portion. A first fitting portion is formed between the first stop blocks and the second stop blocks. A lens is fixed to the frame portion. A second fitting portion is formed on the periphery of the lens. The second fitting portion is fitted into the first fitting portion. Either side of the lens is formed with a retaining hole. A strap is coupled to the lens. Either end of the strap is provided with a coupling member. A raised retaining block is provided on the coupling member. The retaining block is inserted into the retaining hole to be positioned. In this way, the overall volume after being assembled is reduced, and the strength of the connection of the lens and the frame is increased.

In the foregoing patent, the strap is inserted in the retaining hole only with the retaining block. Therefore, when the strap is held on the head, the strap will generate a backward pulling force, which is likely to break the retaining block or to crack the retaining hole. It has disadvantages in use.

Taiwan Utility Model Publication No. M605535 published on Dec. 21, 2020 discloses a device composed of a goggle and a face shield. The goggle is provided with positioning holes and an elastic strap on both sides of the frame. The elastic strap is inserted through the positioning holes to be positioned. The frame of the goggle is provided with a coupling member. The coupling member has a sleeve portion and a blocking portion. Both sides of the face shield are formed with coupling holes. The size of the coupling hole is slightly smaller than that of the blocking portion of the coupling member. The coupling hole of the face shield is coupled to the coupling member of the goggle. The coupling hole of the face shield is engaged in the blocking portion of the coupling member, so that the assembly is completed for use.

The elastic strap of the foregoing patent also generates a backward pulling force that is likely to break or crack the sleeve portion and the blocking portion, so it is not ideal in use.

SUMMARY OF THE INVENTION

In view of the shortcomings of the prior art, the primary object of the present invention is to provide a combined goggle and face mask, comprising a goggle body, a strap, a shield, and two retaining members. Either side of the goggle body is recessed with a receiving portion. The receiving portion has two engaging holes. A front edge of the goggle body is provided with a lens. The receiving portion further has two oblique sides that are adjacent to respective edges of the engaging holes and oblique rearward. The two oblique sides each extend toward the lens and are connected to form a bent side in the form of a curved corner. The strap is coupled to the goggle body. Either end of the strap is provided with a bracket to be coupled to the receiving portion. The bracket is supported by the receiving portion. The bracket has two engaging blocks corresponding in position to the respective engaging holes. The engaging blocks are engaged in the respective engaging holes. The bracket has two first edges that are oblique edges corresponding to the two oblique sides of the receiving portion and two second edges each in the form of a curved corner corresponding to the two bent sides. The shield is coupled to the google body. Each of the retaining members is coupled to the bracket.

Preferably, the bracket further has a retaining hole. Each retaining member includes a pair of raised retaining portions that can be elastically retracted and extended. The retaining portions are inserted and secured in the retaining hole.

Preferably, either side of the shield has a retaining end. The retaining end is formed with a perforation. The retaining portions are inserted and secured in the perforation.

Preferably, the bracket further has two stop flanges arranged around the retaining hole. The two retaining portions each have a protruding block. When the corresponding retaining member is rotated relative to the bracket, the protruding blocks of the retaining portions are engaged with the stop flanges to prevent the corresponding retaining member from disengaging from the bracket.

Preferably, an outer surface of one of the stop flanges is provided with a stepped slide section, and a protrusion is provided on the other stop flange.

Preferably, one edge of the slide section, adjacent to the retaining hole, is tapered toward another edge of the slide section.

Preferably, the slide section has a through hole.

Preferably, an inner surface of each of the two stop flanges is formed with a recess.

The above technical features have the following advantages:

1. The bracket is supported by the receiving portion, and the two engaging blocks are engaged in the respective engaging holes. The first edges that are oblique edges and the second edges each in the form of a curved corner of the bracket are supported by the two oblique sides and the two bent sides each in the form of a curved corner of the receiving portion, which can offset the backward pulling force. The strap is prevented from being pulled and broken, and the bracket is prevented from cracking under stress, so as to ensure the overall integrity.

2. The outer surface of one of the stop flanges is provided with the stepped slide section to provide a multi-step slide positioning effect, so as to adjust the opening angle of the shield.

3. One edge of the slide section, adjacent to the retaining hole, is tapered toward the other edge of the slide section, and the slide section has the through hole, so that the slide section is more flexible and has certain elasticity.

DETAILED DESCRIPTION OF THE PREFERRED EMBODIMENTS

Embodiments of the present invention will now be described, by way of example only, with reference to the accompanying drawings.

Figure 1:
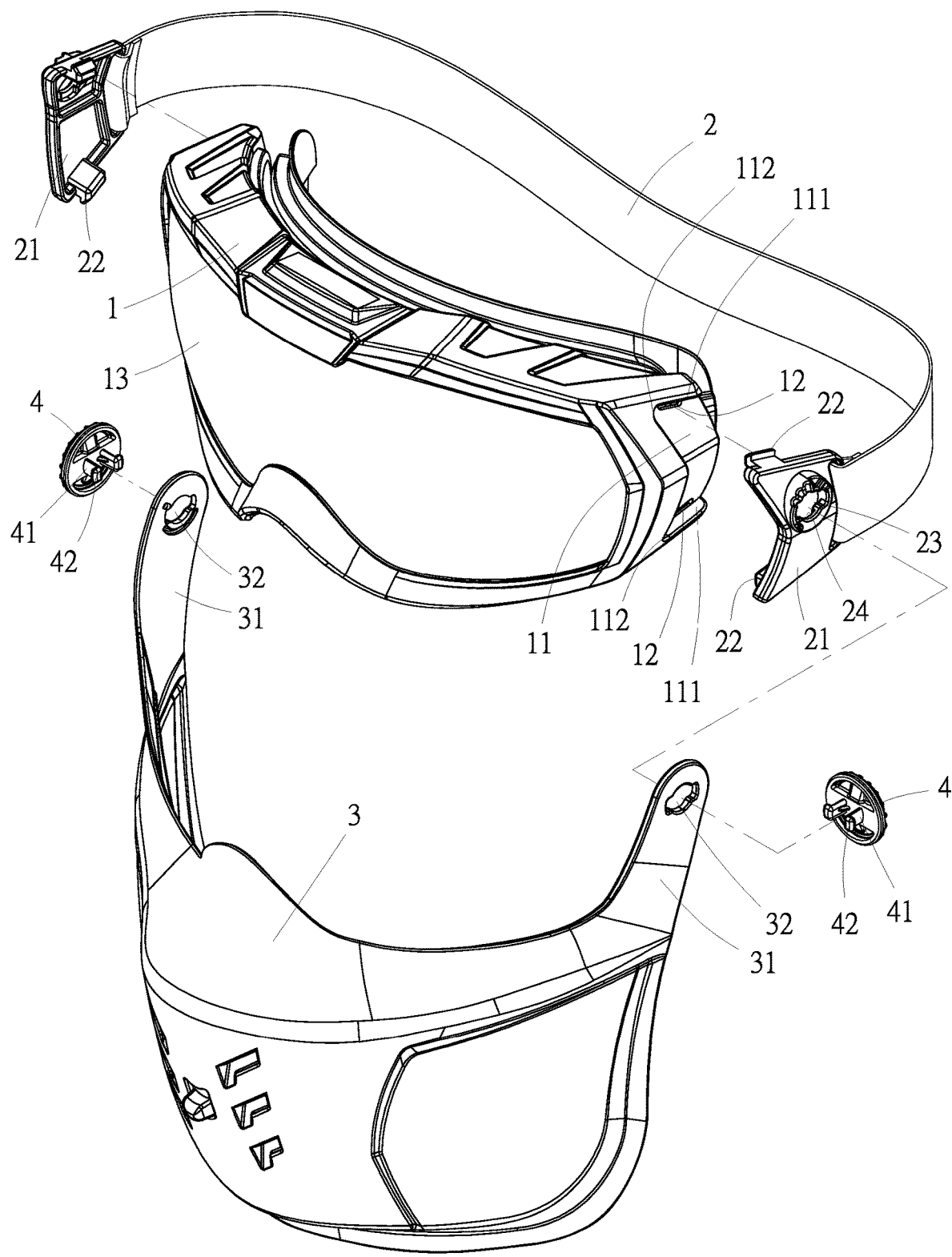
FIG. 1 is an exploded view according to a preferred embodiment of the present invention.
Figure 2:
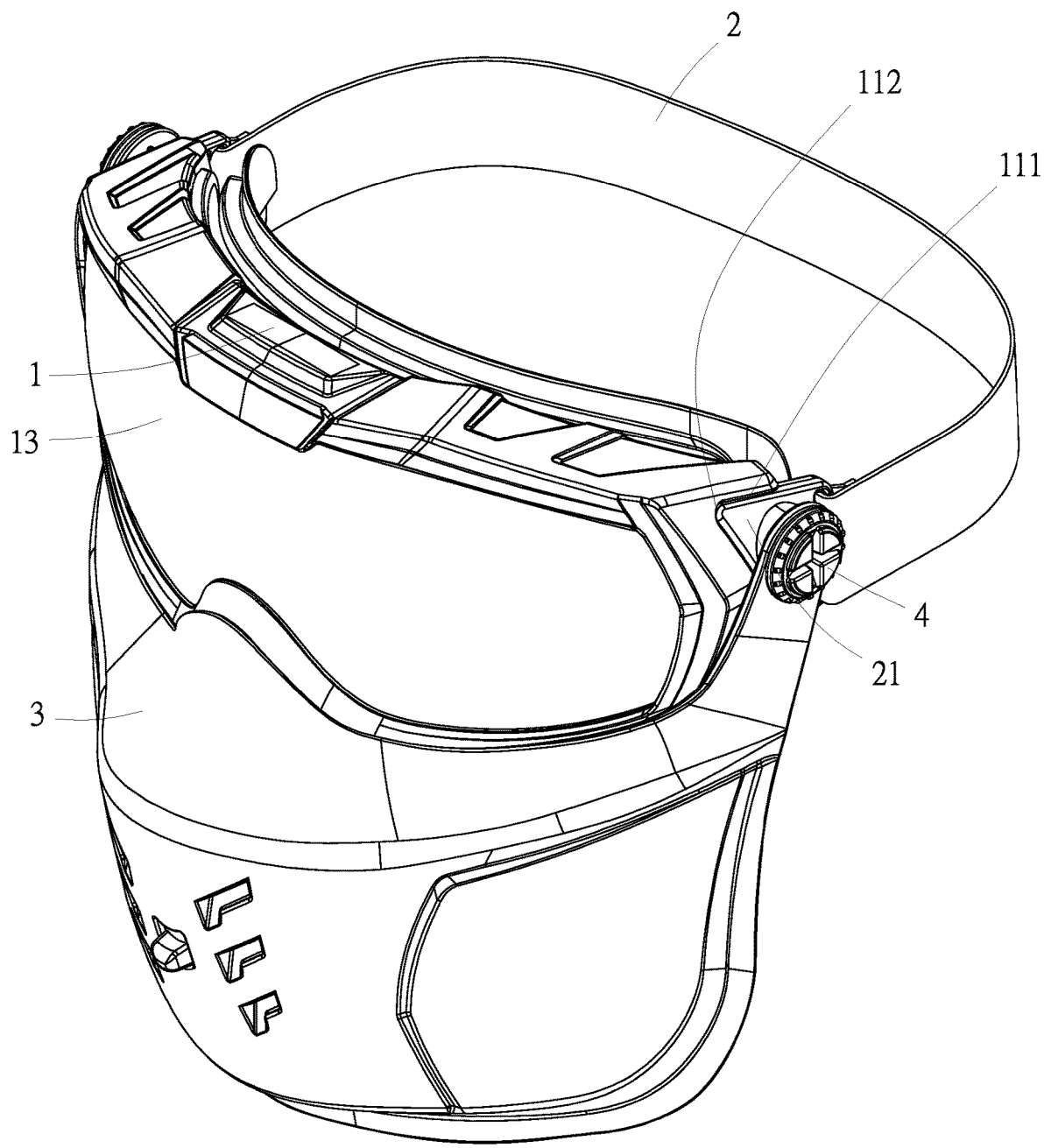
FIG. 2 is a perspective view according to the preferred embodiment of the present invention.

As shown in FIG. 1 and FIG. 2, a combined goggle and face mask according to an embodiment of the present invention comprises a goggle body 1, a strap 2, a shield 3, and two retaining members 4.

Figure 4:
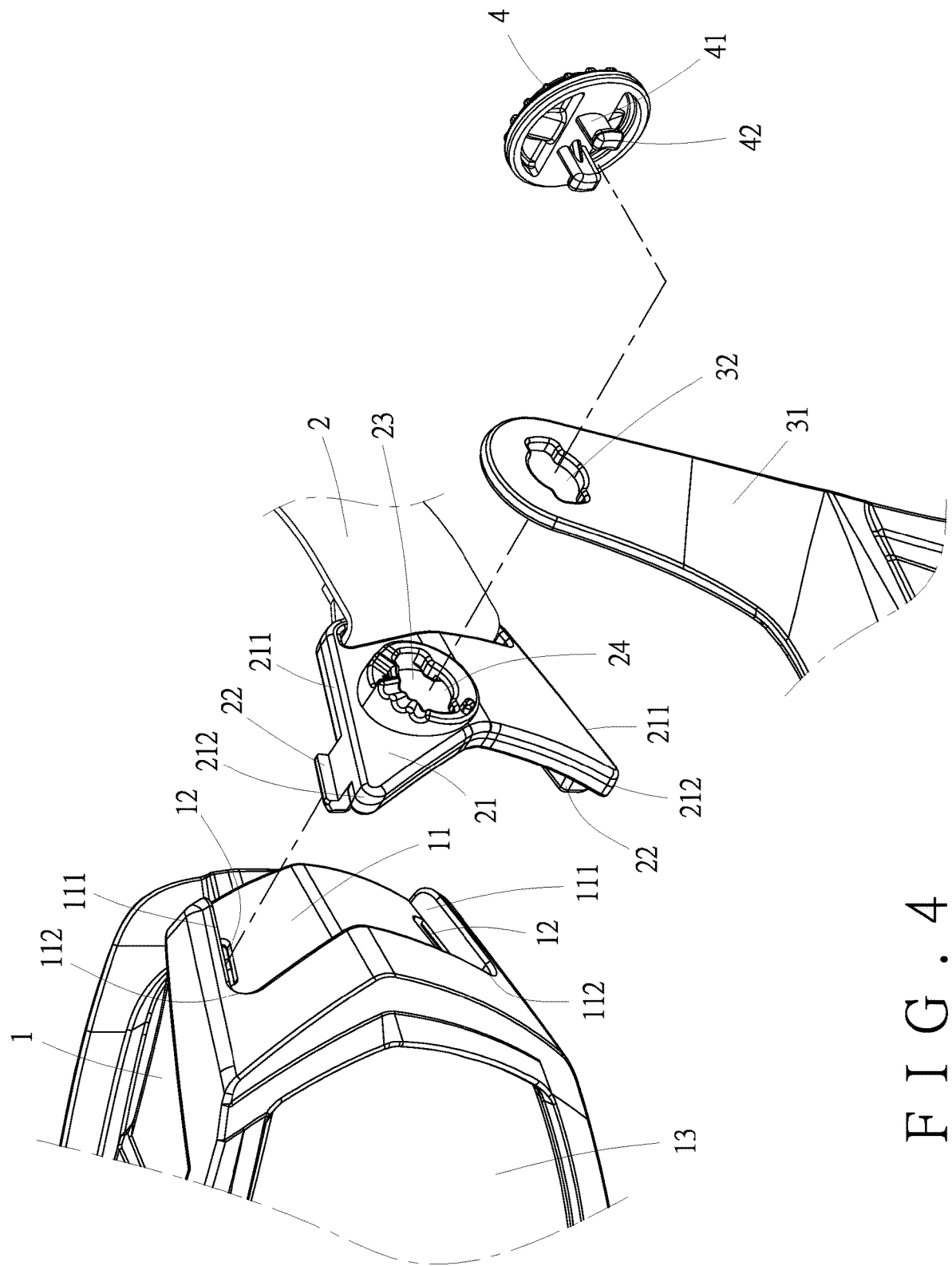
FIG. 4 is an enlarged schematic view of the bracket and the retaining member according to the preferred embodiment of the present invention.
Figure 12:
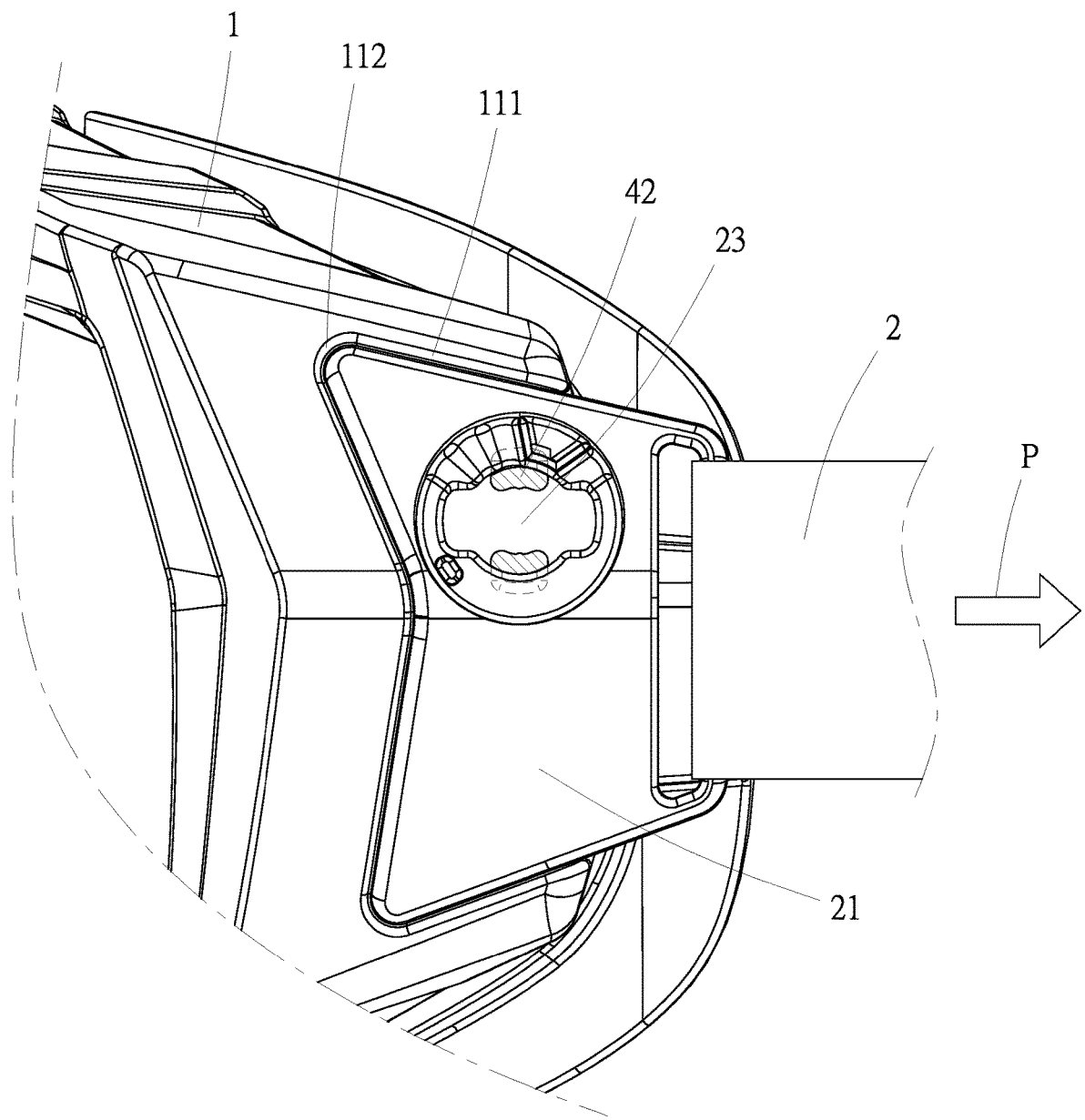
FIG. 12 is a schematic view according to the preferred embodiment of the present invention, showing that a backward pulling force is generated after the bracket is coupled to the receiving portion.

Either side of the goggle body 1 is recessed with a receiving portion 11. The receiving portion 11 has two engaging holes 12. The front edge of the goggle body 1 is provided with a lens 13. As shown in FIG. 4, the receiving portion 11 further has two oblique sides 111 that are adjacent to the respective edges of the engaging holes 12 and oblique rearward (as shown in FIG. 12). The two oblique sides 111 each extend toward the lens 13 and are connected to form a bent side 112 in the form of a curved corner.

Figure 3:
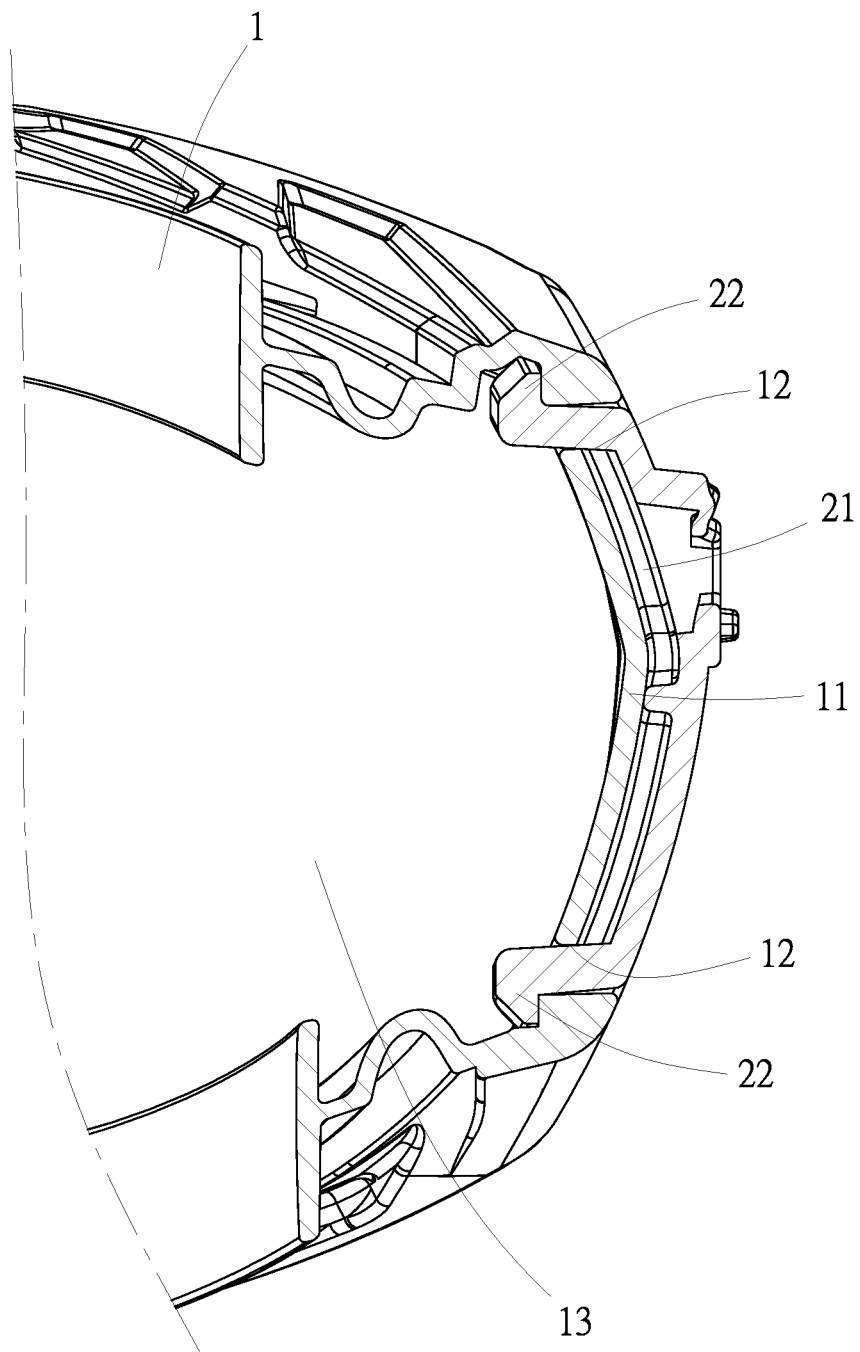
FIG. 3 is a schematic view according to the preferred embodiment of the present invention, showing that the engaging blocks are engaged in the engaging holes.
Figure 7:
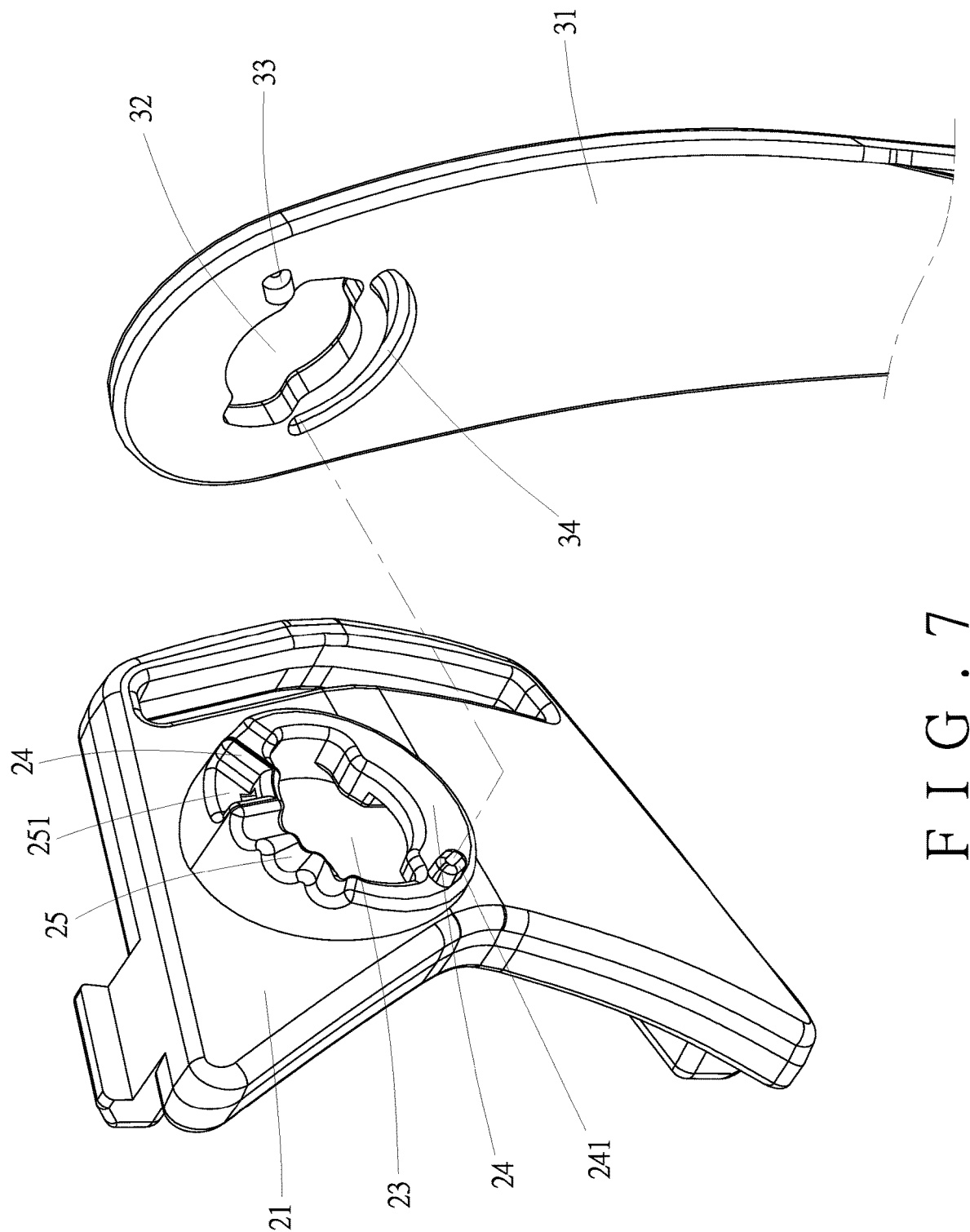
FIG. 7 is an enlarged schematic view of the bracket and the retaining end according to the preferred embodiment of the present invention.
Figure 8:
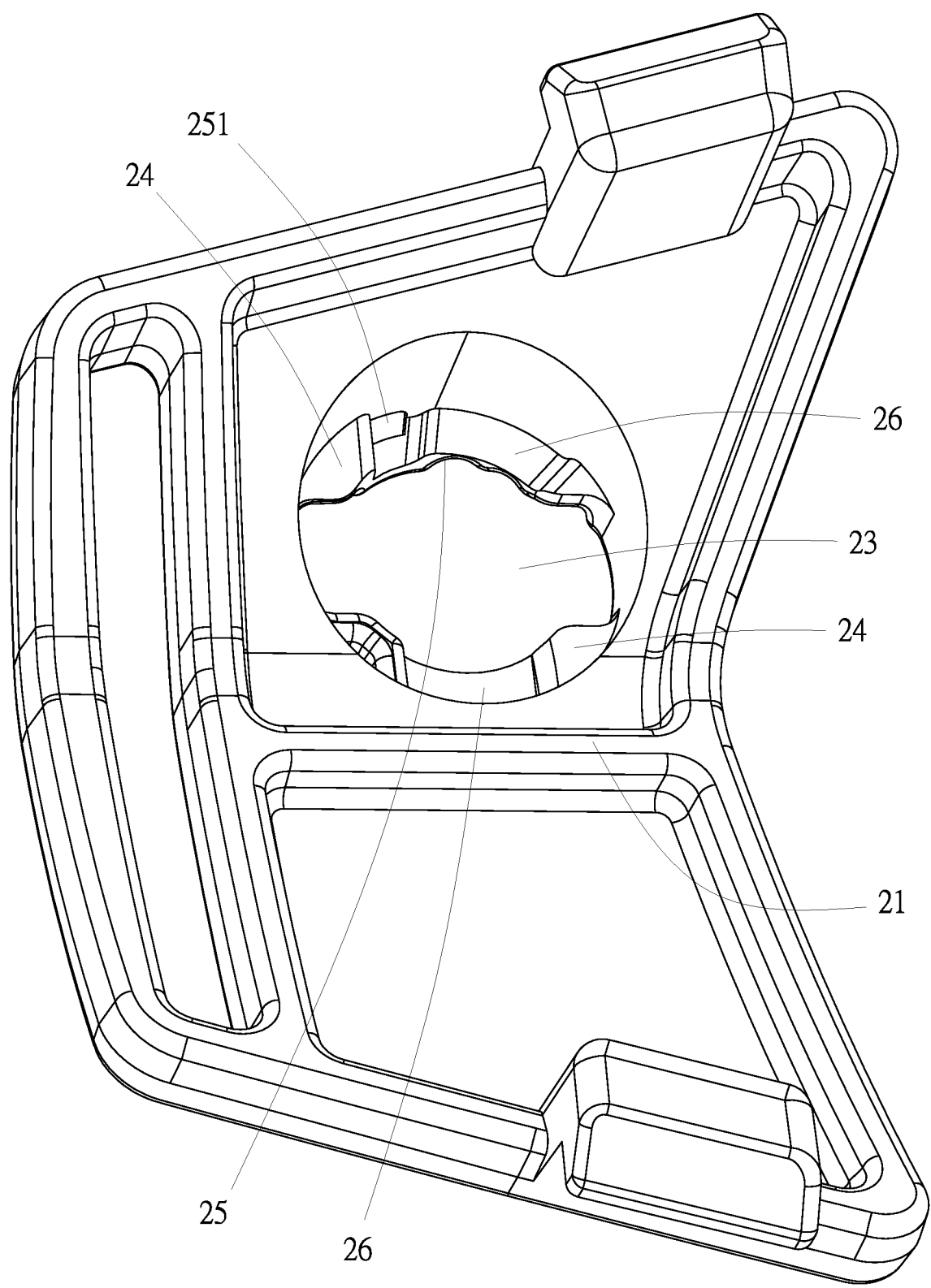
FIG. 8 is an enlarged schematic view of the bracket according to the preferred embodiment of the present invention.
Figure 9:
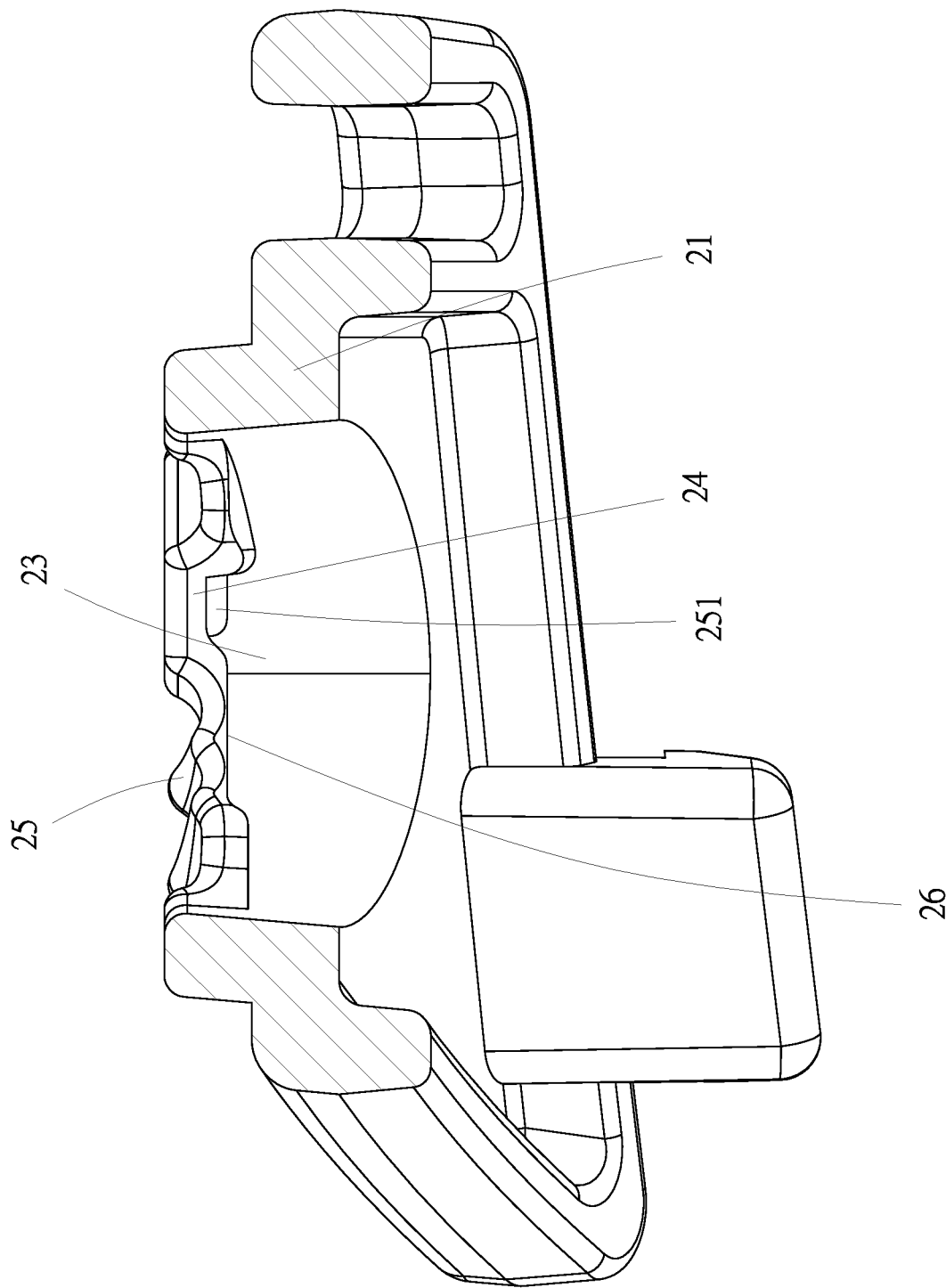
FIG. 9 is a cross-sectional view of the bracket according to the preferred embodiment of the present invention.

The strap 2 is coupled to the goggle body 1. Either end of the strap 2 is provided with a bracket 21 to be coupled to the receiving portion 11. The bracket 21 has two engaging blocks 22 corresponding in position to the respective engaging holes 12. The engaging blocks 22 are engaged in the respective engaging holes 12 (as shown in FIG. 3), so that the bracket 21 is coupled to the receiving portion 11 and is supported by the receiving portion 11. The bracket 21 has two first edges 211 that are oblique edges corresponding to the two oblique sides 111 of the receiving portion 11 and two second edges 212 each in the form of a curved corner corresponding to the two bent sides 112. The bracket 21 further has a retaining hole 23 and two stop flanges 24 arranged around the retaining hole 23. As shown in FIG. 7, the outer surface of one of the stop flanges 24 is provided with a stepped slide section 25, so as to provide a multi-step slide positioning effect. As shown in FIG. 8 and FIG. 9, one edge of the slide section 25, adjacent to the retaining hole 23, is tapered toward the other edge of the slide section 25. The slide section 25 has a through hole 251, so that the slide section 25 is more flexible and has certain elasticity. A protrusion 241 is provided on the other stop flange 24. The inner surface of each of the two stop flanges 24 is formed with a recess 26. The recesses 26 of the two stop flanges 24 face each other.

The shield 3 is coupled to the google body 1. Either side of the shield 3 has a retaining end 31. The retaining end 31 is formed with a perforation 32. The inner surface of the retaining end 31 is provided with a slide block 33 and a slide groove 34 close to the periphery of the perforation 32.

Figure 5:
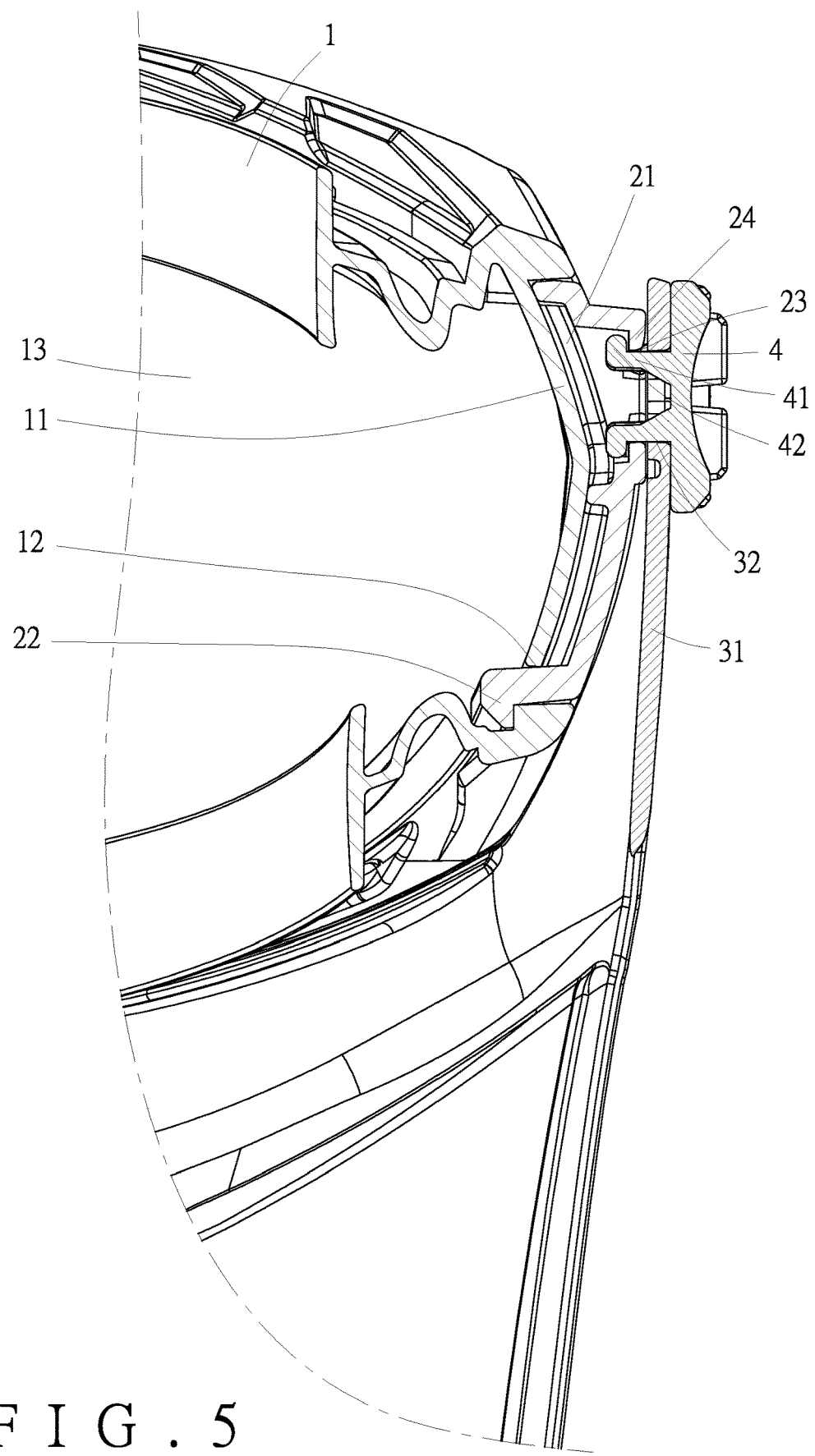
FIG. 5 is a schematic view according to the preferred embodiment of the present invention, showing that the retaining member is coupled to the bracket.
Figure 10:
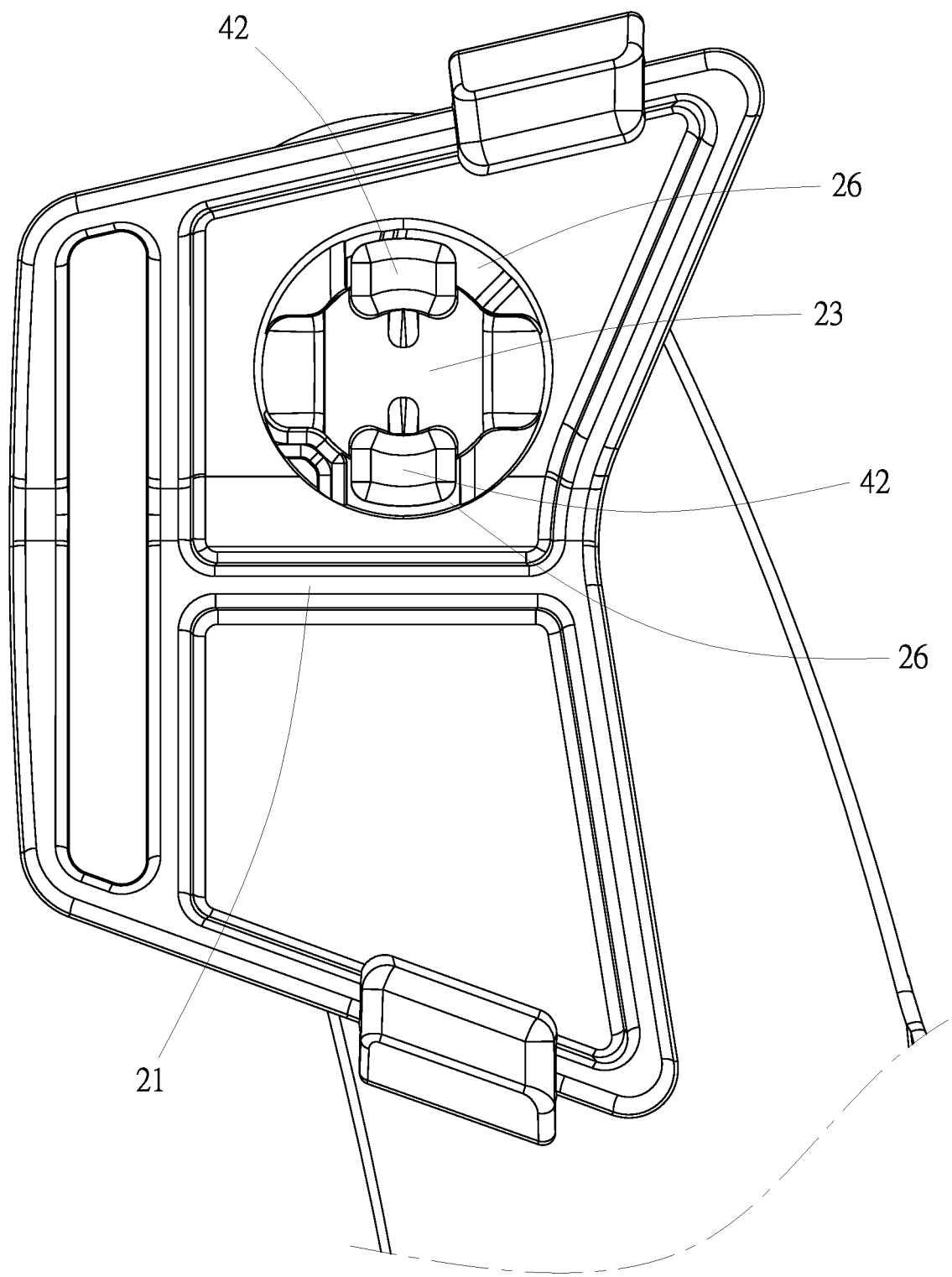
FIG. 10 is a schematic view according to the preferred embodiment of the present invention, showing that the protruding blocks are engaged in the recesses.

The retaining member 4 is inserted and positioned in the retaining hole 23 of the bracket 21 and the perforation 32 of the shield 3. The retaining member 4 includes a pair of raised retaining portions 41 that can be elastically retracted and extended (as shown in FIG. 4). The retaining portions 41 each have a protruding block 42. When the retaining member 4 is rotated relative to the bracket 21, the protruding block 42 is engaged in the recess 26 of the stop flange 24 (as shown in FIG. 5 and FIG. 10) to prevent the retaining member 4 from disengaging from the bracket 21.

Figure 6:
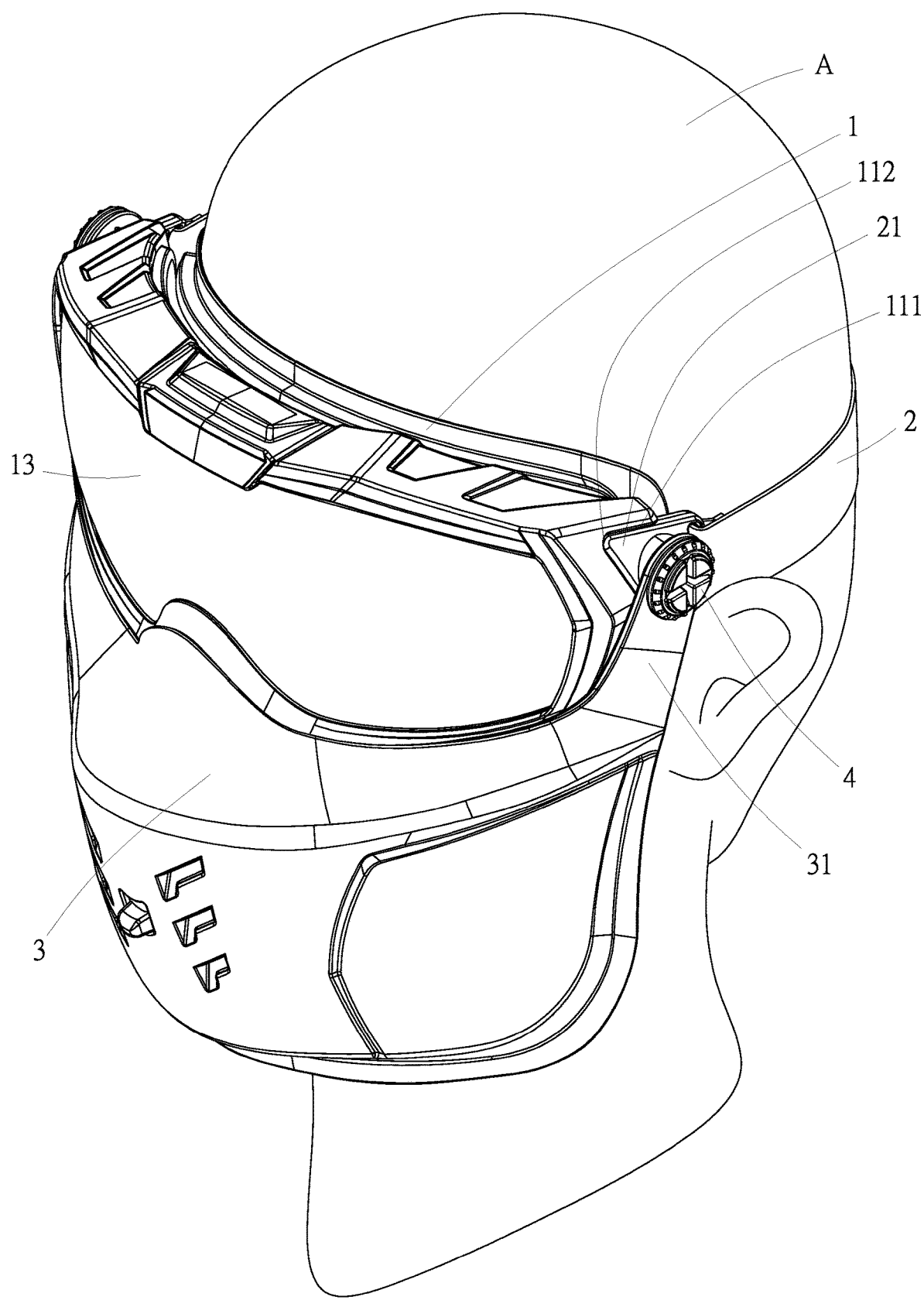
FIG. 6 is a schematic view according to the preferred embodiment of the present invention when in use.
Figure 11:
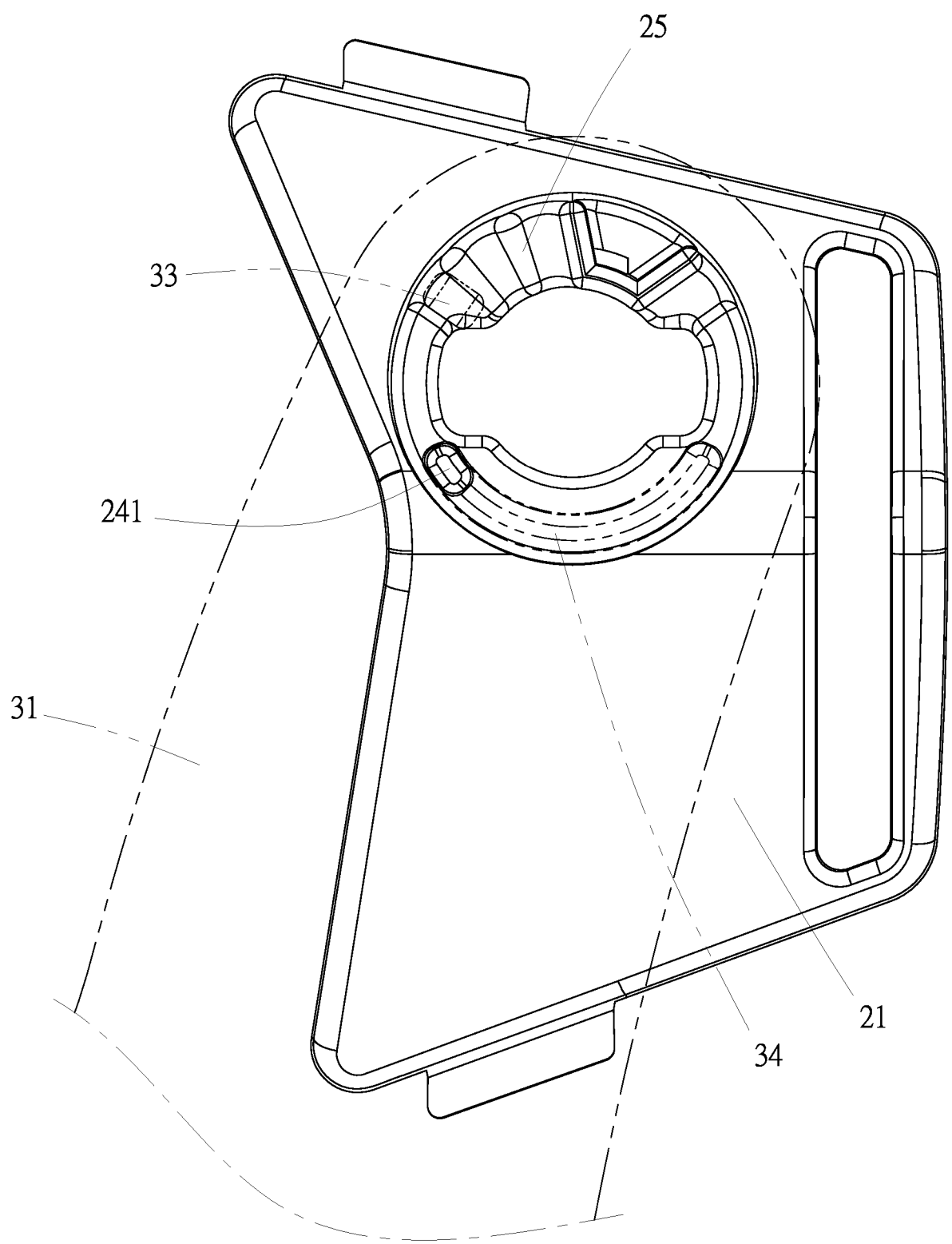
FIG. 11 is a schematic view according to the preferred embodiment of the present invention, showing that the slide block is slid and positioned on the slide section.

In installation, as shown FIG. 1 and FIG. 3, first, the brackets 21 at the two ends of the strap 2 are correspondingly placed in the two receiving portions 11, respectively. The two engaging blocks 22 of each bracket 21 are engaged in the respective engaging holes 12 (as shown in FIG. 3), so that the two brackets 21 are coupled to the two receiving portions 11, respectively. Then, the two retaining ends 31 of the shield 3 correspond to the two brackets 21, and the perforations 32 of the two retaining ends 31 are aligned with the retaining holes 23 of the two brackets 21. The retaining portions 41 of each retaining member 4 (as shown in FIG. 4) are correspondingly inserted into the perforation 32 of the shield 3 and the retaining hole 23 of the bracket 21. When the retaining portions 41 pass through the perforation 32 and the retaining hole 23, they will be compressed to be elastically retracted. After passing through the perforation 32 and the retaining hole 23, the retaining portions 41 will be elastically extended. After that, When the retaining member 4 is rotated relative to the bracket 21, the protruding block 42 is engaged in the recess 26 of the stop flange 24 (as shown in FIG. 5 and FIG. 10) to prevent the retaining member 4 from disengaging from the bracket 21. In this way, the strap 2 is coupled to the goggle body 1. As shown in FIG. 7 and FIG. 11, the slide block 33 is slidable on the slide section 25 to provide a multi-step slide positioning effect. The protrusion 241 is slidable in the slide groove 34, so as to adjust the opening angle of the shield 3 (as shown in FIG. 6).

When in use, the strap 2 is put on the user's head A. As shown in FIG. 1, FIG. 6 and FIG. 12, when the strap 2 is put on the head A, a pulling force P will be generated to the brackets 21 at the two ends of the strap 2. Because the two brackets 21 are received in the respective receiving portions 11 and the two engaging blocks 22 of the two brackets 21 are engaged in the respective engaging holes 12, the two brackets 21 are supported by the two receiving portions 11, in cooperation with the two engaging blocks 22 of the two brackets 21 to be engaged in the respective engaging holes 12. The bracket 21 has the first edges 211 that are oblique edges corresponding to the two oblique sides 111 of the receiving portion 11 and the second edges 212 that are curved corner corresponding to the curved corner of the two bent sides 112. Since the strap 2 is held on the head A of the user, the strap 2 will generate a backward pulling force P. First, the bracket 21 is supported by the two oblique sides 111 and the two bent sides 112 each in the form of a curved corner, which can offset the backward pulling force P. The two engaging blocks 22 are engaged into the engaging holes 12 to provide a fixing effect. Through the first edges 211 that are oblique edges and the second edges 212 each in the form of a curved corner of the bracket 21, the strap 2 is prevented from being pulled and broken, and the bracket 21 is prevented from cracking under stress, so as to ensure the overall integrity and prevent the goggle body 1 from being damaged.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A combined goggle and face mask, comprising:
 a goggle body, either side of the goggle body being recessed with a receiving portion, the receiving portion having two engaging holes, a front edge of the goggle body being provided with a lens, the receiving portion further having two oblique sides that are adjacent to respective edges of the engaging holes and oblique rearward, the two oblique sides each extending toward the lens and being connected to form a bent side in the form of a curved corner;
 a strap, coupled to the goggle body, either end of the strap being provided with a bracket to be coupled to the receiving portion, the bracket being supported by the receiving portion, the bracket having a retaining hole and two engaging blocks corresponding in position to the respective engaging holes, the engaging blocks being engaged in the respective engaging holes, the bracket having two first edges that are oblique edges corresponding to the two oblique sides of the receiving portion and two second edges each in the form of a curved corner corresponding to the two bent sides;
 a shield, coupled to the google body, wherein either side of the shield has a retaining end configured with a perforation; and
 a retaining member coupled to the bracket at said either end of the strap, wherein said retaining member includes a pair of raised retaining portions configured to be elastically retracted and extended, and wherein the raised retaining portions are inserted and secured in the retaining hole of the bracket and in the perforation formed at said retaining end at said either side of the shield.

2. The combined goggle and face mask as claimed in claim 1, wherein the bracket further has two stop flanges arranged around the retaining hole, the two retaining portions each have a protruding block, when the corresponding retaining member is rotated relative to the bracket, the protruding blocks of the retaining portions are engaged with the stop flanges to prevent the corresponding retaining member from disengaging from the bracket.

3. The combined goggle and face mask as claimed in claim 2, wherein an outer surface of one of the stop flanges is provided with a stepped slide section, and a protrusion is provided on the other stop flange.

4. The combined goggle and face mask as claimed in claim 3, wherein one edge of the slide section, adjacent to the retaining hole, is tapered toward another edge of the slide section.

5. The combined goggle and face mask as claimed in claim 3, wherein the slide section has a through hole.

6. The combined goggle and face mask as claimed in claim 2, wherein an inner surface of each of the two stop flanges is formed with a recess.

7. A combined goggle and face mask, comprising:
 a goggle body, either side of the goggle body being recessed with a receiving portion, the receiving portion having two engaging holes, a front edge of the goggle body being provided with a lens, the receiving portion further having two oblique sides that are adjacent to respective edges of the engaging holes and oblique rearward, the two oblique sides each extending toward the lens and being connected to form a bent side in the form of a curved corner;
 a strap, coupled to the goggle body, either end of the strap being provided with a bracket to be coupled to the receiving portion, the bracket being supported by the receiving portion, the bracket having a retaining hole and two engaging blocks corresponding in position to the respective engaging holes, the engaging blocks being engaged in the respective engaging holes, the bracket having two first edges that are oblique edges corresponding to the two oblique sides of the receiving portion and two second edges each in the form of a curved corner corresponding to the two bent sides;
 a shield, coupled to the google body; and
 a retaining member coupled to the bracket at said either end of the strap, wherein said retaining member includes a pair of raised retaining portions configured to be elastically retracted and extended, wherein the raised retaining portions are inserted and secured in the retaining hole of the bracket at said either side of the shield, and wherein the bracket further has two stop flanges arranged around the retaining hole, each of the pair of raised retaining portions having a protruding block, when the corresponding retaining member is rotated relative to the bracket, the protruding blocks of the retaining portions are engaged with the stop flanges to prevent the corresponding retaining member from disengaging from the bracket.

\* \* \* \* \*